US012383261B1

(12) United States Patent
Ayub (10) Patent No.: US 12,383,261 B1
(45) Date of Patent: Aug. 12, 2025

(54) FOUR-LEGGED STAPLE SYSTEM FOR MEDICAL STAPLERS

(71) Applicant: Hamid Ayub, Plantation, FL (US)

(72) Inventor: Hamid Ayub, Plantation, FL (US)

( * ) Notice: Subject to any disclaimer, the term of this patent is extended or adjusted under 35 U.S.C. 154(b) by 24 days.

(21) Appl. No.: 18/945,770

(22) Filed: Nov. 13, 2024

Related U.S. Application Data (63) Continuation-in-part of application No. 18/438,478, filed on Feb. 11, 2024, now Pat. No. 12,089,840.

(51) Int. Cl.
| | | |
|---|---|---|
| *A61B 17/068* | (2006.01) | |
| *A61B 17/064* | (2006.01) | |
| *A61B 17/072* | (2006.01) | |
| *A61B 90/00* | (2016.01) | |
| *A61B 17/00* | (2006.01) | |

(52) U.S. Cl.
CPC ...... *A61B 17/0684* (2013.01); *A61B 17/0644* (2013.01); *A61B 17/07207* (2013.01); *A61B 90/08* (2016.02); *A61B 90/39* (2016.02); *A61B 2017/00836* (2013.01); *A61B 2017/00862* (2013.01); *A61B 2017/00942* (2013.01); *A61B 2017/00946* (2013.01); *A61B 2017/0641* (2013.01); *A61B 2017/0688* (2013.01); *A61B 2017/07235* (2013.01); *A61B 2090/0807* (2016.02); *A61B 2090/3937* (2016.02)

(58) Field of Classification Search
CPC ... A61B 17/068; A61B 17/064; B25C 5/1603; B25C 5/025
See application file for complete search history.

(56) References Cited

U.S. PATENT DOCUMENTS

| | | | | |
|---|---|---|---|---|
| 4,467,805 A | * | 8/1984 | Fukuda | A61B 17/0684 606/217 |
| 4,610,251 A | * | 9/1986 | Kumar | A61B 17/0644 411/460 |
| 6,076,720 A | * | 6/2000 | Deng | B25C 5/1603 227/123 |
| 6,726,695 B2 | * | 4/2004 | Tong | A61B 17/068 606/151 |
| 8,801,753 B2 | * | 8/2014 | Bender | A61B 17/11 606/220 |
| 2012/0085809 A1 | * | 4/2012 | Milo | A61B 17/0644 227/181.1 |
| 2012/0175401 A1 | * | 7/2012 | Bachman | A61B 17/0682 227/177.1 |

* cited by examiner

*Primary Examiner* — Nathaniel C Chukwurah (57) ABSTRACT

The present invention introduces a medical stapler configured for efficient wound and incision closure with cosmetically appealing end result, Utilizing a four-legged staple and a single-track dispensing mechanism. The medical stapler enables rapid deployment of staples in a vertical mattress suture fashion, facilitating optimal tissue approximation without the requirement of suturing. The deployment mechanism is designed to affect a staggered release of the fine legs and the standard legs of each staple, thereby promoting engagement with superficial tissue layers and engagement with deeper tissue layers. Additionally, the staple assembly allows for independent deployment of the fine legs from the standard legs as needed, enhancing procedural efficiency and flexibility.

9 Claims, 7 Drawing Sheets

FOUR-LEGGED STAPLE SYSTEM FOR MEDICAL STAPLERS

CROSS-REFERENCE TO RELATED APPLICATION

This application is a Continuation-in-Part (CIP) of U.S. patent Ser. No. 12/089,840 B2, filed on 11 Feb. 2024 and issued Sep. 17, 2024, the disclosure of which is hereby incorporated by reference in its entirety.

FIELD OF INVENTION

Embodiments of a present disclosure relate to the field of surgical instruments and more particularly to a surgical medical stapler.

BACKGROUND

In surgical procedures, effective wound and incision closure is critical for reducing anaesthesia time and improving patient outcomes. Conventional suturing techniques frequently necessitate multiple steps and the use of suture, introducing complexity. Existing stapling devices have made strides in addressing these challenges, yet limitations persist in terms of procedural efficiency, and adaptability to diverse surgical scenarios.

Many prior art solutions lack the capability to provide multi-sized staple legs within a single device, which can result in suboptimal tissue alignment and a cosmetically less appealing outcome. Consequently, there is an unmet need for a medical stapler that overcomes these limitations, facilitating a more efficient and appealing effective wound and incision closure.

SUMMARY

The present invention provides a medical stapler designed to enhance the efficiency and cosmetically appealing end result of the wound and incision closure. The medical stapler incorporates a four-legged staple configuration that provides improved tissue alignment compared to traditional staplers, resulting in better closure and a more aesthetically pleasing outcome. The staple is dispensed through a single-track mechanism, which simplifies the deployment process and reduces the number of steps typically required in surgical suturing of incision or wound.

The deployment mechanism of the medical stapler is engineered to facilitate a staggered release of the staple legs, specifically allowing the fine legs to be deployed slightly ahead of the standard legs or the standard legs are deployed slightly ahead the fine legs. This design promotes engagement with superficial tissue layers, ensuring that the fine legs anchor the superficial tissue and the standard legs secure deeper layers. This sequential deployment is instrumental in achieving optimal alignment and tissue approximation, thereby enhancing cosmetically appealing end result of the wound and incision closure and reducing overall surgical and anaesthesia time.

Additionally, the staple assembly is configured to allow for the independent deployment of the fine legs from the standard legs when desired. This feature provides surgeons with greater flexibility during surgical procedures, enabling tailored closure techniques based on the specific needs of the wound or incision closure. Such adaptability is particularly beneficial in complex surgical environments where varying tissue types and thicknesses are encountered. Furthermore, the design of the medical stapler emphasizes a reduction in procedure time. The medical stapler streamlines the closure process by eliminating the need for traditional suturing, which is commonly required in vertical mattress suture closure.

This efficiency not only contributes to reduce surgical times but can also enhance patient comfort and recovery by minimizing the duration of the procedure.

Overall, the invention represents a significant advancement in the field of surgical wound closure. The medical stapler enhances the closure process by combining innovative features such as a four-legged staple design, a staggered release mechanism, and independent deployment capability. The medical stapler addresses existing challenges in prior art devices, ultimately leading to improved surgical outcomes and patient comfort.

BRIEF DESCRIPTION OF DRAWINGS

The disclosure will be described and explained with additional specificity and detail with the accompanying figures in which:

FIG. 1 A is a schematic diagram illustrating Four-Legged Single Staple Design for Wound and incision Closure, in accordance with embodiment of the present disclosure.

FIG. 1 B is a sequential arrangement of the four-legged staples, presented as a staple strip, in accordance with embodiment of the present disclosure.

FIGS. 2A and 2 B presents medical stapler featuring enclosed body with staples and staple count indicator, in accordance with embodiment of the present disclosure.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION OF THE DISCLOSURE

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated system, and such further applications of the principles of the disclosure as would normally occur to those skilled in the art are to be construed as being within the scope of the present disclosure. It will be understood by those skilled in the art that the foregoing general description and the following detailed descriptions are exemplary and explanatory of the disclosure and are not intended to be restrictive thereof.

Unless otherwise defined, all technical and scientific terms used herein have the same meaning as commonly understood by those skilled in the art to which this disclosure belongs and in the surgical and medical field. The system, methods, and examples provided herein are only illustrative and not intended to be limiting.

This present invention discloses a medical stapler designed specifically for wound and incision closure, featuring an innovative four-legged staple assembly that significantly enhances its functionality and versatility in surgical applications. Each four-legged staple within the assembly is uniquely structured, comprising a pair of fine legs and a pair of standard legs, tailored to address varying tissue closure needs effectively. The fine legs of the staple are engineered for the closure of superficial tissue layers. Their reduced size and delicate construction allow for minimal trauma to the epidermal and dermal tissues during deployment. This feature is crucial for ensuring an aesthetic and gentle closure, which is particularly important where the appearance of the skin is desirable for patient recovery. In contrast, the standard legs of the staple are designed for the closure of deeper tissue layers. These legs are standard and sturdier, providing robust anchoring within the underlying tissue structures. This design enables reliable fixation and support for the healing process, ensuring that the wound and incision edges remain securely approximated even under stress. One of the standout features of this four-legged staple assembly is its capability to achieve simultaneous closure across multiple tissue depths with a single deployment action. This functionality streamlines the stapling process, allowing for quicker and more efficient closure of complex wounds and incision that may involve both superficial and deeper tissue layers. This design eliminates the need for multiple stapling actions, saving time during surgical procedures and promoting better healing outcomes for patients.

Figure 1:
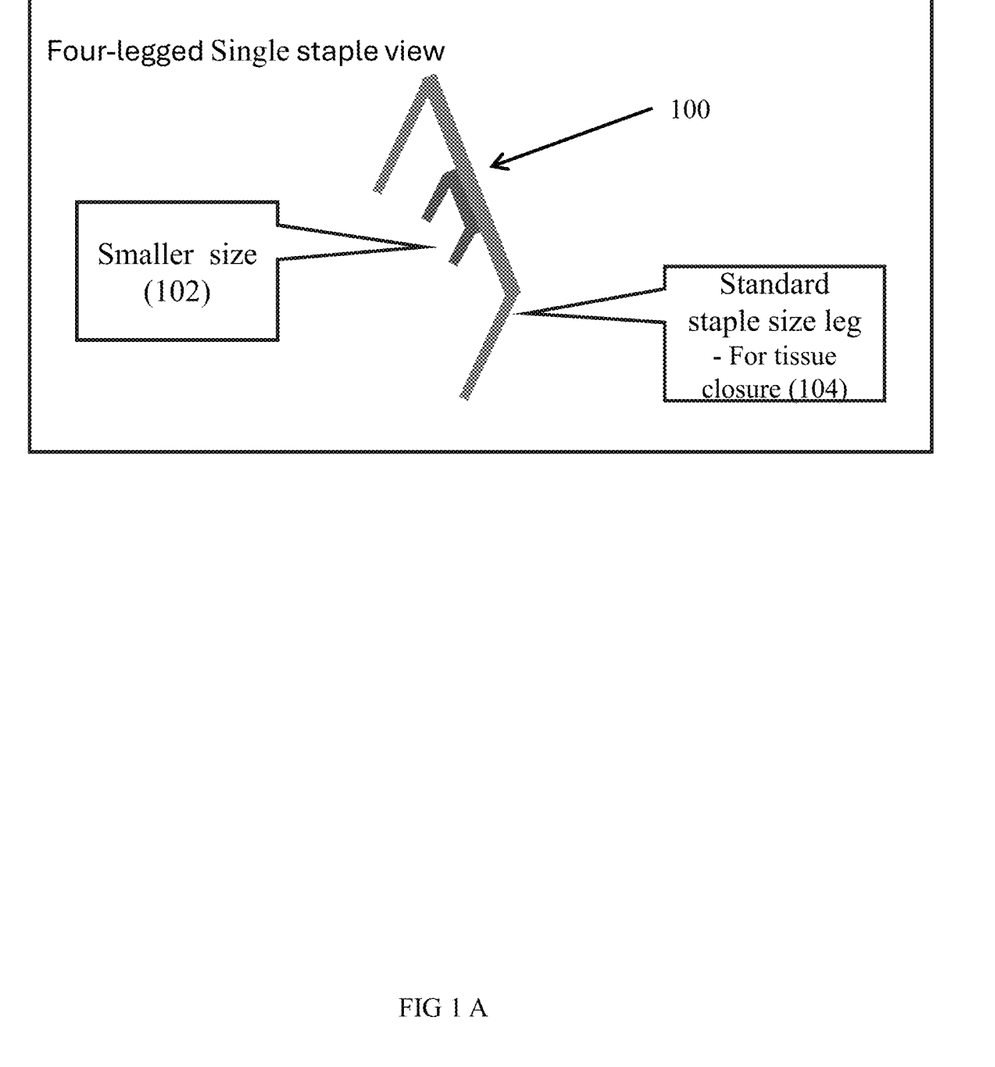

FIG. 1 A is a schematic diagram illustrating Four-Legged Single Staple Design (100) for wound and incision Closure, in accordance with embodiment of the present disclosure. This figure presents a novel surgical staple featuring a four-legged configuration, designed to optimize the closure of wounds with enhanced precision. The key components of the staple are as follows:

Smaller Size Staple Legs (102): The staple comprises a pair of shorter and finer legs, specifically engineered for the closure of superficial skin layers. These legs are intentionally designed to be reduced in length and diameter, allowing for a gentler insertion into the epidermal and dermal tissues. The finer structure of these legs minimizes the risk of excessive trauma, ensuring a more aesthetically pleasing wound and incision closure while promoting faster healing of the superficial layers. This feature is particularly advantageous in cosmetic and minimally invasive procedures where preserving the integrity of the skin is paramount.

Standard Staple Legs (104): Accompanying the smaller legs are a pair of standard and sturdier legs that are crafted for the secure closure of deeper tissue layers. The robust construction of these legs provides a strong anchoring mechanism within the underlying tissue structures, ensuring reliable wound and incision closure that withstands the stresses of healing and movement. The elongated design allows for optimal penetration into deeper tissues, effectively securing the wound edges and promoting optimal tissue alignment during the healing process.

FIG. 1 B is a sequential arrangement of the four-legged staples, presented as a staple strip, in accordance with embodiment of the present disclosure. The figure also illustrates a sequential arrangement of the four-legged staples, presented as a staple strip. This innovative configuration allows for straightforward loading and dispensing of the staples within a surgical stapling device, enhancing the efficiency of wound and incision closure procedures. The staple strip design ensures that multiple staples can be delivered in rapid succession, facilitating quick and effective closure of wounds without the need for manual reloading or repositioning of individual staples.

This four-legged staple design is intended to enable the simultaneous closure of both superficial and deeper tissue layers with a single application. This staple design enhances the precision, stability, and efficiency of wound and incision closure procedures by combining the distinct advantages of shorter, finer legs for surface closure with standard, sturdier legs for deeper anchorage. The dual-leg configuration not only streamlines the surgical process but also promotes optimal healing outcomes, reducing the likelihood of excessive scar tissue formation-associated with traditional wound closure methods.

The design specifications of the staples are tailored for optimal performance in surgical applications. Each fine leg of the four-legged staple is designed with a length ranging from 3 mm to 8 mm, specifically configured for engagement with superficial tissue layers. This shorter length minimizes tissue trauma while ensuring effective closure. On the other hand, each standard leg has a length ranging from 8 mm to 16 mm, providing secure anchoring within deeper tissue layers. This differentiation in leg lengths allows for the efficient closure of wounds that involve various tissue depths, ensuring that each staple effectively fulfils its intended function within the surgical procedure.

In another embodiment, the medical stapler is designed to allow for the independent deployment of the fine legs from the standard legs of the staple assembly, providing surgeons with the flexibility to adapt their stapling technique to the specific requirements of the surgical procedure. For example, when prioritizing the closure of superficial layers, the fine legs can be deployed independently to achieve optimal tissue alignment without immediately engaging the standard legs. This capability enhances the precision of the closure and gives surgeons greater control over the stapling process, effectively accommodating various tissue types and closure needs. The four-legged staple assembly incorporates two distinct types of legs-fine and standard-which can be easily separated for independent deployment. This allows the surgeon to choose whether to use the fine legs for delicate tissue handling or to deploy both the fine and standard legs together for a stronger hold in areas requiring additional support. This selective deployment ultimately improves control and precision during procedures, enhancing the stapler's versatility in different surgical applications.

In an embodiment, the medical stapler includes a special deployment mechanism designed to release the fine and standard legs of each four-legged staple in a staggered manner. This mechanism allows the fine legs to be released slightly before the standard legs, so they can engage the more superficial tissue layers first. This sequence helps to secure the outer tissue layers initially, followed by a deeper engagement as the standard legs deploy, promoting a more controlled and layered tissue closure.

In another embodiment, the medical stapler includes a deployment mechanism that enables a staggered release of the fine and standard legs of each four-legged staple, with the standard legs deploying slightly ahead of the fine legs. This allows the standard legs to engage and secure the deeper tissue layers first, followed by the engagement of the fine legs with the more superficial layers. This sequence aims to achieve a stable, multi-layered tissue closure, ensuring that both deep and surface layers are appropriately secured.

Figure 2:
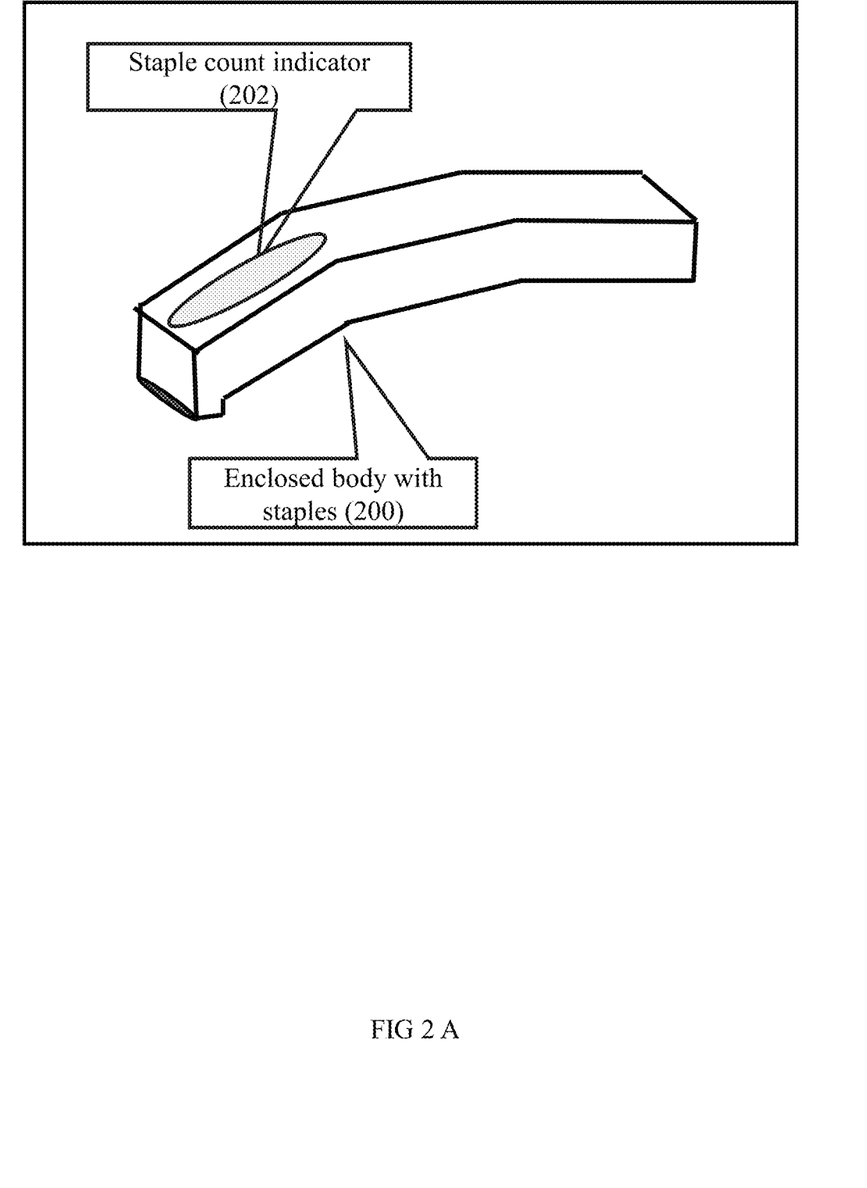

FIGS. 2A and 2 B presents medical stapler featuring enclosed body with staples (200) and staple count indicator (202), in accordance with embodiment of the present disclosure. The enclosed body with staples (200) is a critical component of the surgical stapler, designed to securely house the staples while facilitating their efficient deployment during surgical procedures. This body is constructed as a closed compartment, which prevents accidental dislodgment or contamination of the staples before they are used. Maintaining the sterility of the staples is essential for reducing the risk of infection in surgical settings, making this design element vital for patient safety. The enclosed body also features an efficient loading mechanism that allows for seamless insertion and alignment of the staple strip within the stapler. This ensures that the staples are positioned accurately for deployment, minimizing the likelihood of misfires or uneven staple placement, which could compromise wound and incision closure. When the stapler is activated, the enclosed body enables rapid and precise movement of the staples into the appropriate position for insertion into the tissue. This streamlined deployment process allows for quick successive deployments, which is especially important in time-sensitive surgical environments. The design may also include transparent or semi-transparent sections that allow users to visually confirm the presence of staples without needing to disassemble the device. This visual confirmation enhances user confidence in the device's readiness for use and contributes to a more efficient surgical workflow. The staple count indicator (202) is an essential feature located at the top or on the side of the surgical stapler, enhancing the device's usability and functionality. The indicator incorporates a series of clearly defined markings or indicators along the staple track. These markings serve as a visual guide for surgeons and healthcare providers, enabling them to easily identify the number of staples remaining in the device during deployment. This feature is particularly beneficial as it allows for effective monitoring of staple availability without the need for manual counting or opening the stapler, thereby improving the surgical workflow. As staples are used, the indicator tracks the deployment of each staple, to reflect the remaining count. This dynamic tracking reduces the risk of miscounting or unexpectedly running out of staples during a procedure, which can lead to delays and complications. The ergonomic design ensures that the indicator is easily visible throughout the procedure, allowing for quick glances without disrupting the surgical process. The staple count indicator significantly enhances the efficiency and effectiveness of surgical stapling operations by providing essential information about staple availability at a glance.

Figure 3A:
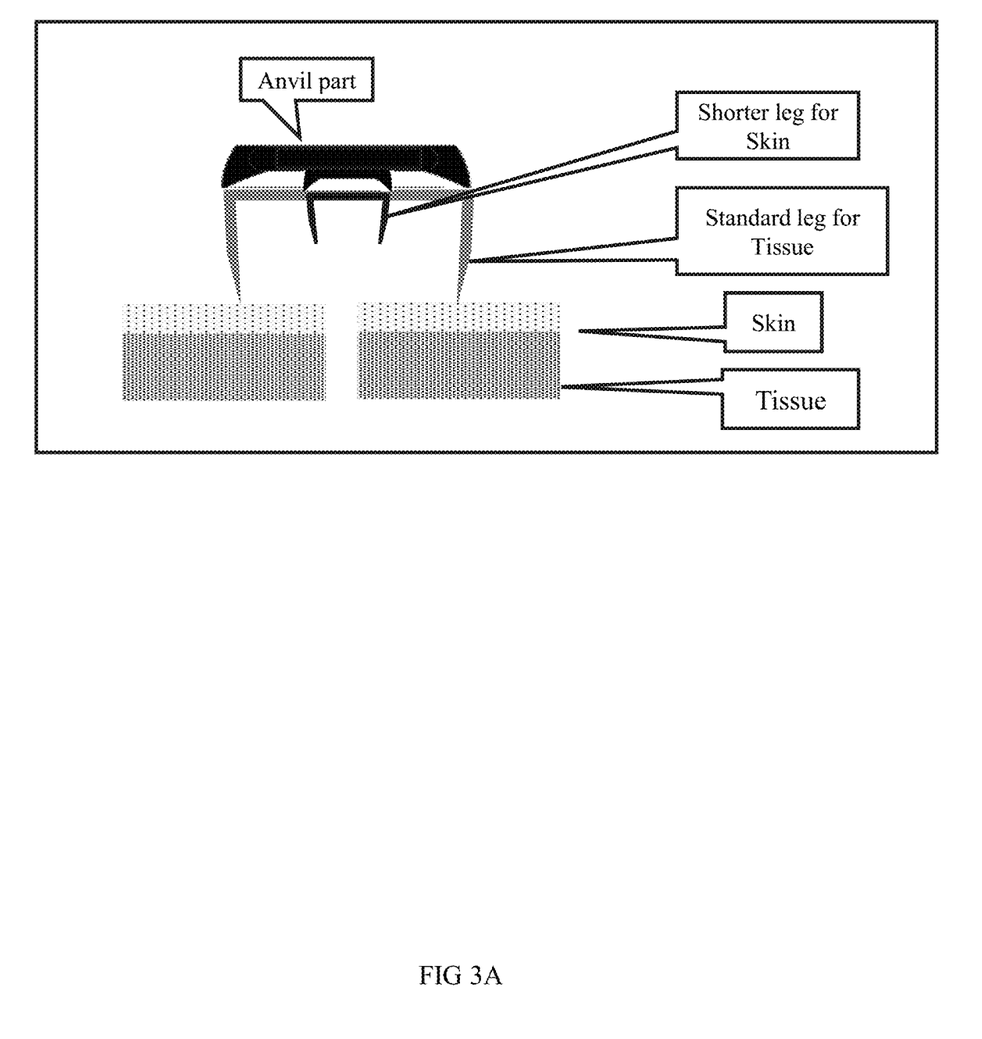
FIG. 3A is a sectional view of surgical stapler deployment mechanism illustrating tissue and skin interaction, in accordance with embodiment of the present disclosure.

FIG. 3 is a sectional view of surgical stapler deployment mechanism illustrating tissue and skin interaction, in accordance with embodiment of the present disclosure. It provides a cross-sectional view of the surgical stapler during the deployment process, emphasizing the interaction between the staple and various layers of tissue. The diagram highlights the distinct anatomical components involved in wound and incision closure, including both the underlying tissue and the outer skin layer. The figure illustrates one of the staple's standard legs penetrating into the deeper tissue layers. This leg is specifically engineered for robust anchoring within the underlying tissue structures, ensuring a secure and effective closure of the wound and incision. Its length and sturdy design facilitate reliable fixation in deeper tissue, which is essential for maintaining the integrity of the wound during the healing process. Adjacent to the deeper tissue layer, the figure shows the staple's shorter leg interacting with the skin layer. This shorter leg is designed for optimal closure at the skin level, allowing for a gentle and precise approximation of the skin edges. This leg aids in achieving an aesthetically pleasing closure while promoting faster healing of the superficial layers. At the top of the figure, the anvil part of the stapler is depicted. The anvil serves as a supportive surface against which the staple is deployed, ensuring proper penetration and placement into both the skin and tissue layers. Its design is critical for providing stability during the stapling process, enabling accurate deployment of the staple and enhancing the overall effectiveness of wound and incision closure.

Figure 3B:
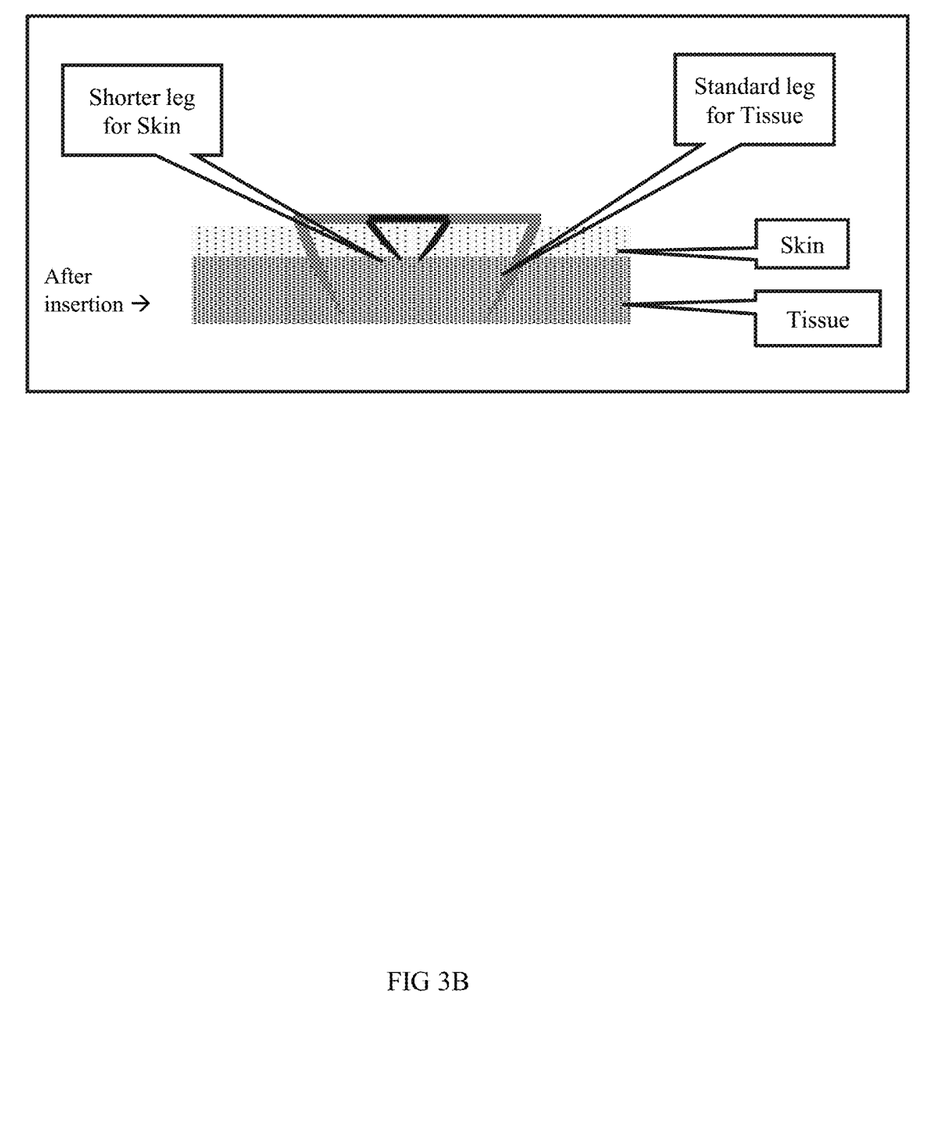
FIG. 3B is a post-insertion view of surgical stapler deployment highlighting tissue and skin interaction, in accordance with embodiment of the present disclosure.

FIG. 3B is a post-insertion view of surgical stapler deployment highlighting tissue and skin interaction, in accordance with embodiment of the present disclosure. In this figure, one of the staple's standard legs is prominently displayed as it securely penetrates into the deeper layers of tissue. This design feature is crucial for ensuring robust anchoring within the underlying structures, which is essential for maintaining the integrity of the wound. The standard leg effectively grasps the tissue, providing a strong hold that supports the healing process by keeping the wound and incision edges together. Alongside the standard leg, the figure depicts the staple's shorter leg interacting with the outer skin layer. This shorter leg is specifically designed to ensure optimal closure at the skin level, effectively approximating the skin edges. This leg contributes to a clean and aesthetically pleasing closure while promoting healing in the superficial layers by minimizing trauma and preventing excessive tension.

Figure 4:
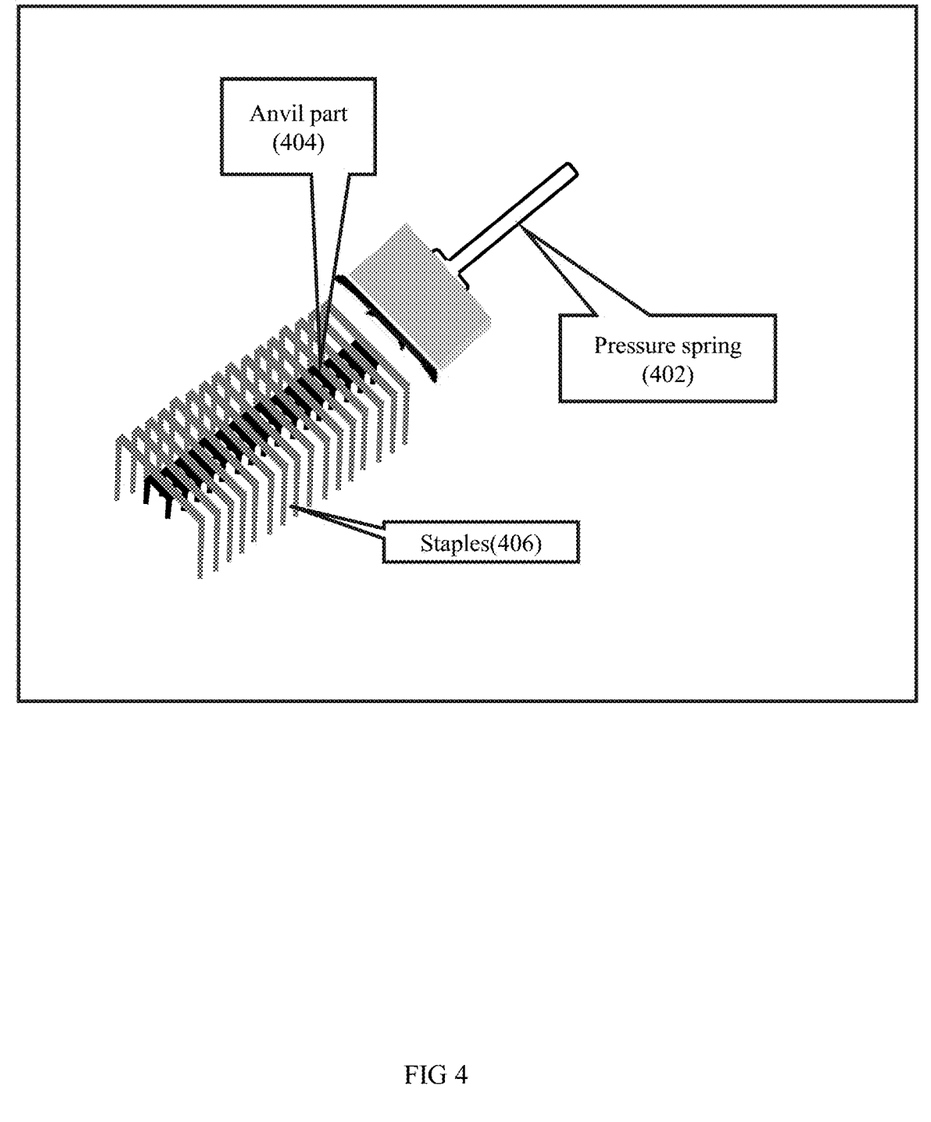
FIG. 4 is a schematic diagram illustrating the assembly of critical components within the medical stapler, as described in accordance with an embodiment of the present disclosure.

FIG. 4 is a schematic diagram illustrating the assembly of critical components within the medical stapler, as described in accordance with an embodiment of the present disclosure. The pressure spring (402) is depicted as a key component of the stapler assembly, designed to provide the necessary force for deploying the staples during the closure of incisions. This spring is specifically engineered to accommodate the distinct requirements of both standard (larger) and fine (smaller) staples. Adjusting the tension and compression of the spring allows the medical stapler to ensure consistent and reliable staple deployment, contributing to effective wound and incision closure. The design of the pressure spring enhances the overall functionality of the stapler by allowing for smooth and controlled operation, which is crucial in surgical environments. The anvil part (404) is illustrated in the diagram as the surface against which the staples are deployed. The anvil's design allows it to provide stability during the stapling process, enabling accurate positioning of the staples as they are driven into the tissue. Its presence is essential for achieving optimal staple penetration and ensuring that the staples effectively secure the tissue layers together. The assembly of staples (406) within the medical stapler, including both standard (larger) staples and fine (smaller) staples is presented. These staples are positioned in a manner that allows for seamless loading and deployment. The inclusion of different staple sizes enables the medical stapler to be versatile, catering to various surgical needs by allowing the surgeon to choose the appropriate staple type for the specific tissue being closed. The staples' design is engineered to provide secure anchorage in the tissue, ensuring reliable wound and incision closure and promoting optimal healing.

In an innovative embodiment, the medical stapler features a single staple track specifically engineered to retain and dispense four-legged staples. This unique configuration is crucial as can enable the concurrent deployment of both the fine and standard legs of each staple, optimizing the stapling process. This single staple track facilitates efficient wound and incision closure across various tissue depths with a single deployment action by enabling simultaneous release. This streamlined approach significantly minimizes the time spent on closure procedures and reduces the risk of complications that can arise from multiple stapling actions. As a result, surgeons can achieve faster and more effective closures, promoting better surgical outcomes for patients.

To further enhance its functionality, the medical stapler is equipped with a deployment mechanism that allows for the staggered release of the fine and standard legs of each four-legged staple This innovative mechanism is designed so that the fine legs are released slightly ahead of the standard legs during deployment, or the standard legs are deployed slightly ahead the fine legs. This staggered release enable the medical practitioner higher flexibility as needed.

The design of the four-legged staple, combined with the single-track dispensing mechanism, significantly reduces procedural time in surgeries. This efficiency is particularly advantageous when performing wound and incision closures in a vertical mattress suture configuration without the need for suturing. The vertical mattress suture technique is recognized for its effectiveness in approximating tissue edges while providing excellent tension distribution across the wound. Utilizing this advanced stapler allows surgeons to achieve the same benefits as the vertical mattress suture configuration quickly and effectively, eliminating the time-consuming and often tedious steps involved in traditional suturing. This not only streamlines the surgical procedure but also minimizes the overall time the patient remains under anaesthesia, thereby enhancing safety and comfort during the operation.

In addition to its advanced deployment features, each four-legged staple is constructed from biocompatible materials selected from a range of options including stainless steel, titanium, and bio-absorbable materials. The choice of these materials is critical to ensure compatibility with the natural healing processes of the body while also minimizing the risk of adverse biological responses. Stainless steel and titanium staples provide durability and strength, making them ideal for secure anchoring in deeper tissue layers. In contrast, bio-absorbable materials offer the advantage of gradual absorption by the body, eliminating the need for additional removal procedures and further enhancing patient comfort.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open-ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present disclosure are intended to be illustrative, but not limiting, of the scope of the invention, which is set forth in the following claims.

What is claimed is:

1. A medical stapler for wound and incision closure, comprising:
   a four-legged staple assembly, wherein each four-legged staple comprises:
   a first staple having a pair of fine legs configured for closure of superficial tissue layers; and
   a second staple having a pair of standard legs configured for closure of deeper tissue layers;
   wherein the first and the second staples together are adapted to achieve closure across multiple tissue depths upon deployment action;
   wherein the staple assembly comprises fine legs and standard legs that are configured to be separable, enabling independent deployment of the fine legs and the standard legs as desired.

2. The medical stapler of claim 1, further comprising:
   a single staple track configured to retain and dispense the four-legged staples, wherein the single staple track enables the deployment of both the fine legs and the standard legs of each four-legged staple, providing efficient wound and incision closure across varying tissue depths when deployed.

3. The medical stapler of claim 1, further comprising a deployment mechanism for staggered release of the fine and standard legs of each four-legged staple, releasing the fine legs slightly ahead of the standard legs to engage superficial tissue layers before deeper layers.

4. The medical stapler of claim 1, further comprising a deployment mechanism for staggered release of the fine and standard legs of each four-legged staple, releasing the standard legs slightly ahead of the fine legs to engage deeper tissue layers before superficial layers.

5. The medical stapler of claim 1, wherein each four-legged staple is composed of a biocompatible material selected from the group consisting of stainless steel, titanium, and bio absorbable materials to ensure compatibility with tissue healing processes and reduce the risk of adverse biological responses.

6. The medical stapler of claim 1, wherein each fine leg of the four-legged staple has a length in the range of 3 mm to 8 mm, configured for superficial tissue engagement, and each standard leg has a length in the range of 8 mm to 16 mm, configured for secure anchoring within deeper tissue layers.

7. The medical stapler of claim 1, wherein the staple assembly allows for the independent deployment of the fine legs from the standard legs when desired.

8. The medical stapler of claim 1, wherein the four-legged staple and single-track dispensing mechanism reduce procedural time, facilitating efficient wound and incision closure in a vertical mattress suture configuration without suturing.

9. The medical stapler of claim 1, further comprising markings or indicators on the staple track for identifying the staple number during deployment.

* * * * *